US012622916B2

(12) United States Patent
Cotman et al.

(10) Patent No.: US 12,622,916 B2
(45) Date of Patent: *May 12, 2026

(54) USE OF H3K9ME3 MODULATION FOR ENHANCING COGNITIVE FUNCTION

(71) Applicant: THE REGENTS OF THE UNIVERSITY OF CALIFORNIA, Oakland, CA (US)

(72) Inventors: Carl Cotman, Santa Ana, CA (US); Larry Overman, Corona del Mar, CA (US); Shikha Snigdha, Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/441,939

(22) Filed: Feb. 14, 2024

(65) Prior Publication Data

US 2024/0374608 A1 Nov. 14, 2024

Related U.S. Application Data

(63) Continuation of application No. 17/697,893, filed on Mar. 17, 2022, now abandoned, which is a continuation of application No. 17/072,539, filed on Oct. 16, 2020, now Pat. No. 11,311,551, which is a continuation of application No. 16/354,996, filed on Mar. 15, 2019, now Pat. No. 10,849,910, which is a continuation of application No. 15/580,419, filed as application No. PCT/US2016/035764 on Jun. 3, 2016, now Pat. No. 10,272,093.

(60) Provisional application No. 62/172,690, filed on Jun. 8, 2015.

(51) Int. Cl.

| | |
|---|---|
| *A61K 31/548* | (2006.01) |
| *A61K 31/202* | (2006.01) |
| *A61K 31/27* | (2006.01) |
| *A61K 31/445* | (2006.01) |
| *A61K 31/473* | (2006.01) |
| *A61K 31/522* | (2006.01) |
| *A61K 45/06* | (2006.01) |
| *A61P 25/00* | (2006.01) |
| *A61P 25/22* | (2006.01) |
| *A61P 25/28* | (2006.01) |
| *C07D 513/18* | (2006.01) |

(52) U.S. Cl.
CPC .......... *A61K 31/548* (2013.01); *A61K 31/202* (2013.01); *A61K 31/27* (2013.01); *A61K 31/445* (2013.01); *A61K 31/473* (2013.01); *A61K 31/522* (2013.01); *A61K 45/06* (2013.01); *A61P 25/00* (2018.01); *A61P 25/22* (2018.01); *A61P 25/28* (2018.01); *C07D 513/18* (2013.01)

(58) Field of Classification Search
CPC .... A61K 31/548; A61K 31/202; A61K 31/27; A61K 31/445; A61K 31/473; A61K 31/522; A61K 45/06; C07D 513/18; A61P 25/28; A61P 25/22; A61P 25/00
USPC ....................................... 514/222.8
See application file for complete search history.

(56) References Cited

U.S. PATENT DOCUMENTS

| | | | | |
|---|---|---|---|---|
| 10,272,093 | B2 * | 4/2019 | Cotman | ................. A61P 25/22 |
| 10,849,910 | B2 * | 12/2020 | Cotman | .............. A61K 31/473 |
| 11,311,551 | B2 * | 4/2022 | Cotman | .............. A61K 31/473 |

FOREIGN PATENT DOCUMENTS

WO WO-2014066435 A1 * 5/2014 ........... A61K 31/548

* cited by examiner

*Primary Examiner* — Kristin A Vajda
(74) *Attorney, Agent, or Firm* — Cotman IP Law group

(57) ABSTRACT

Use of H3K9me3 modulation for enhancing cognitive function and treating anxiety related disorders is presented. A composition is administered to the subject comprising a therapeutically effective amount of a SUV39H1 inhibitor comprising analogs of ETP69. The therapeutically effective amount is effective in treating cognitive dysfunction in aging and age-related disorders.

20 Claims, 11 Drawing Sheets

ETP69

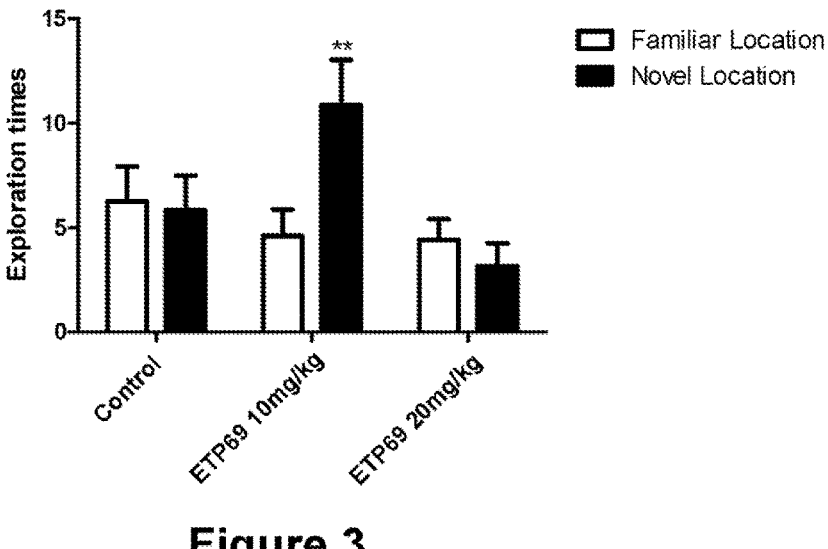
Figure 3
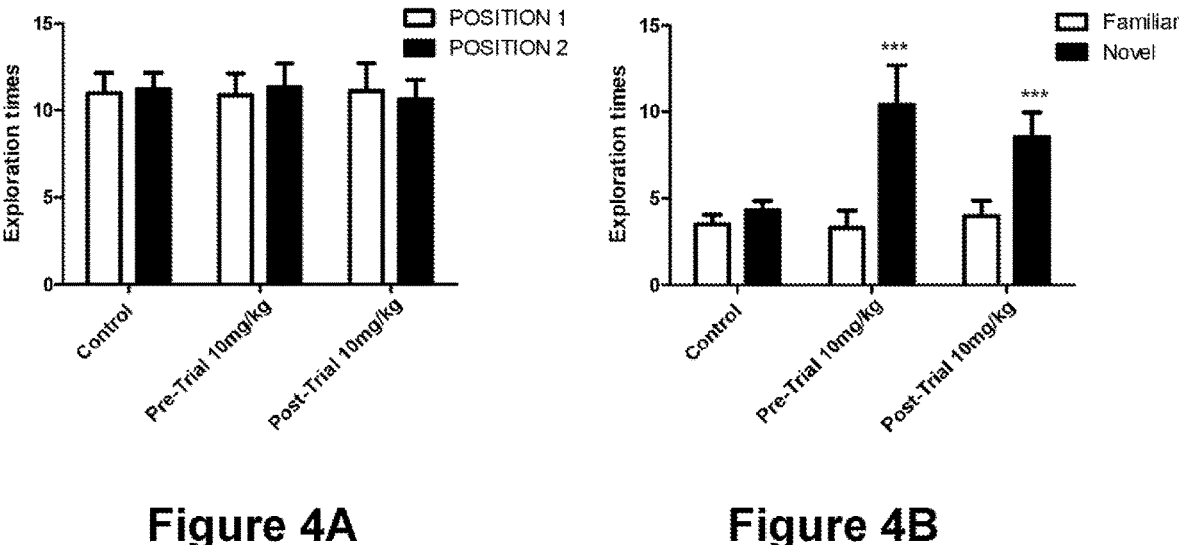
Figure 4A                          Figure 4B

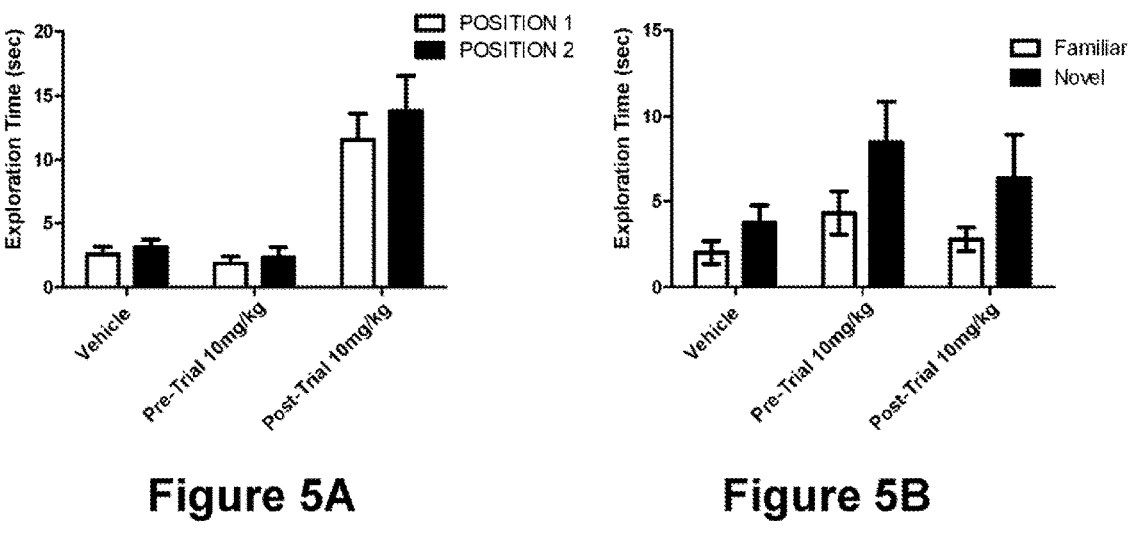
Figure 5A                    Figure 5B
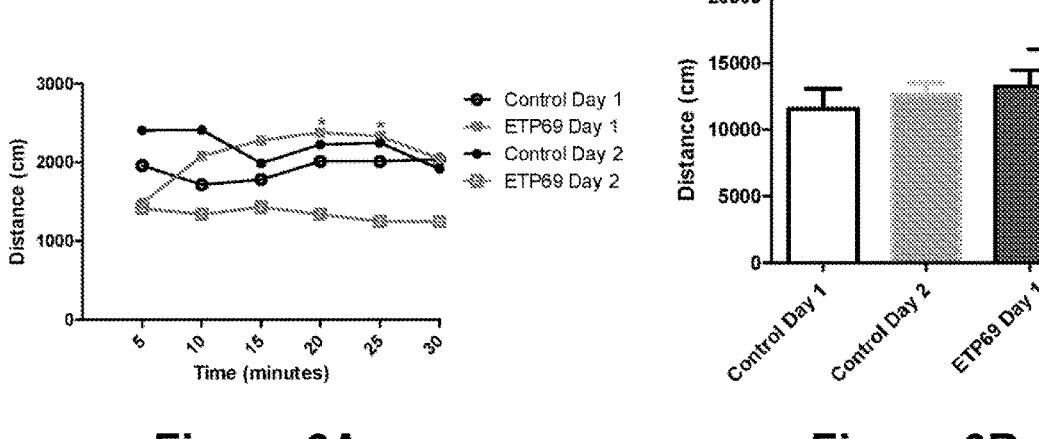
Figure 6A                    Figure 6B

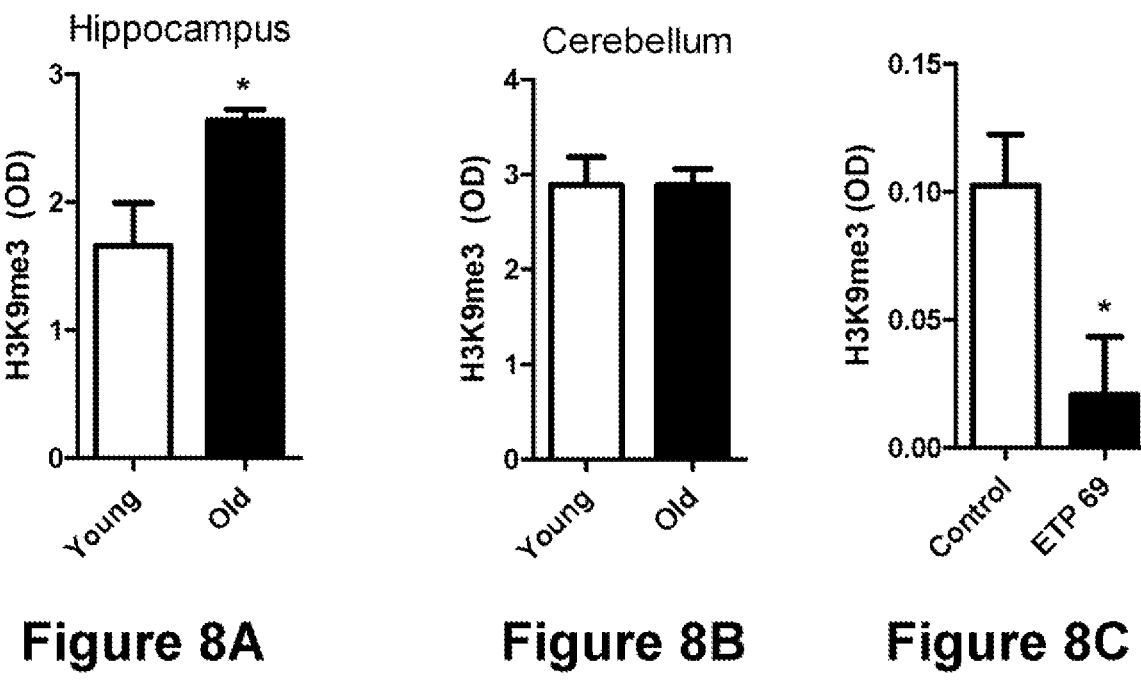
Figure 8A          Figure 8B          Figure 8C
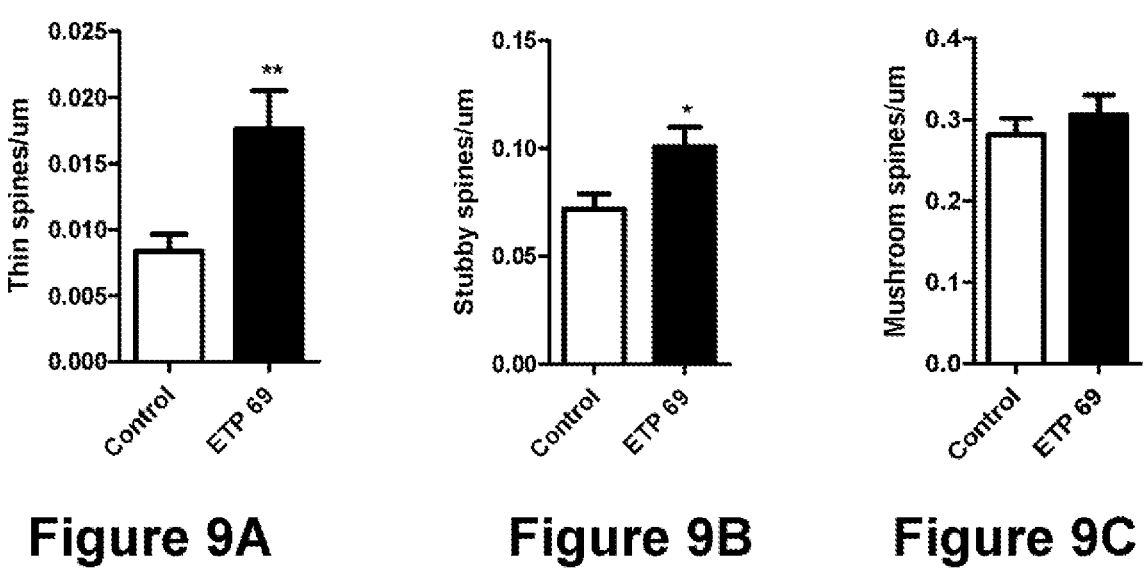
Figure 9A          Figure 9B          Figure 9C

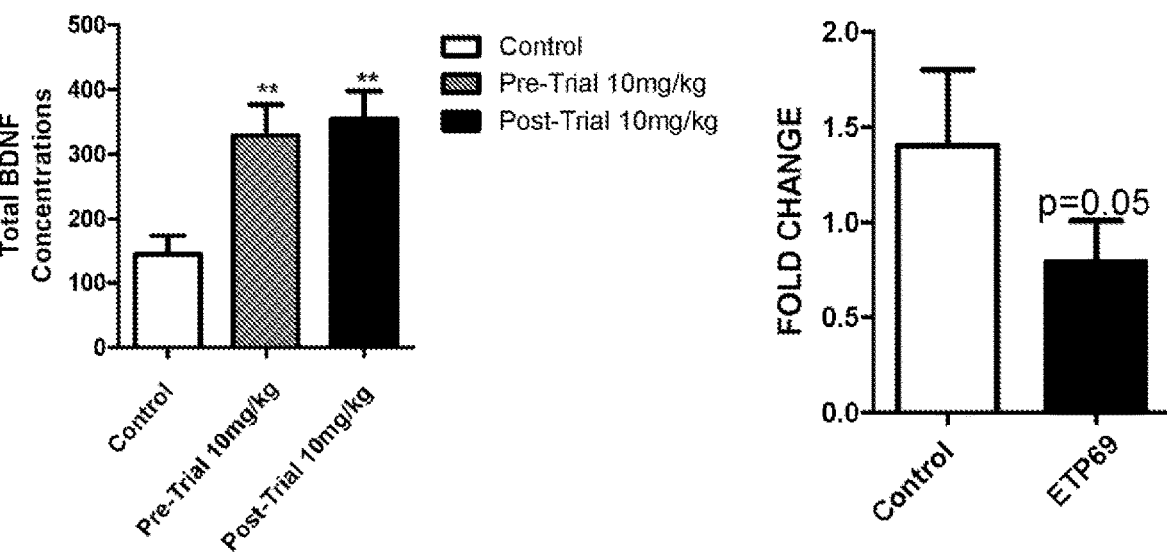
Figure 12A                    Figure 12B
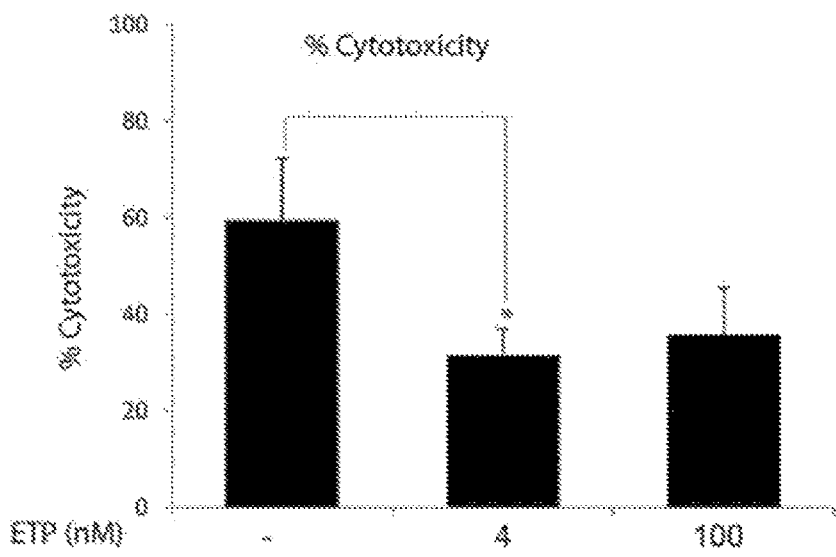
Figure 13

A
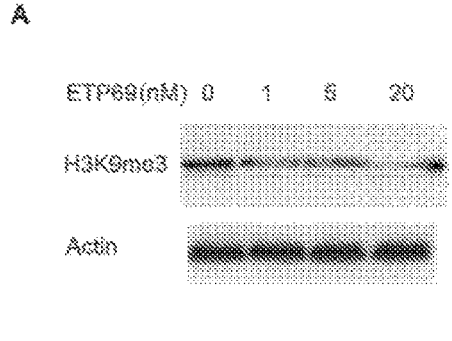
B
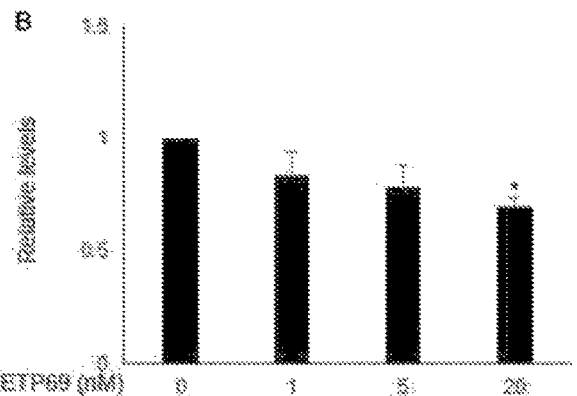
Figure 14A                                   Figure 14B

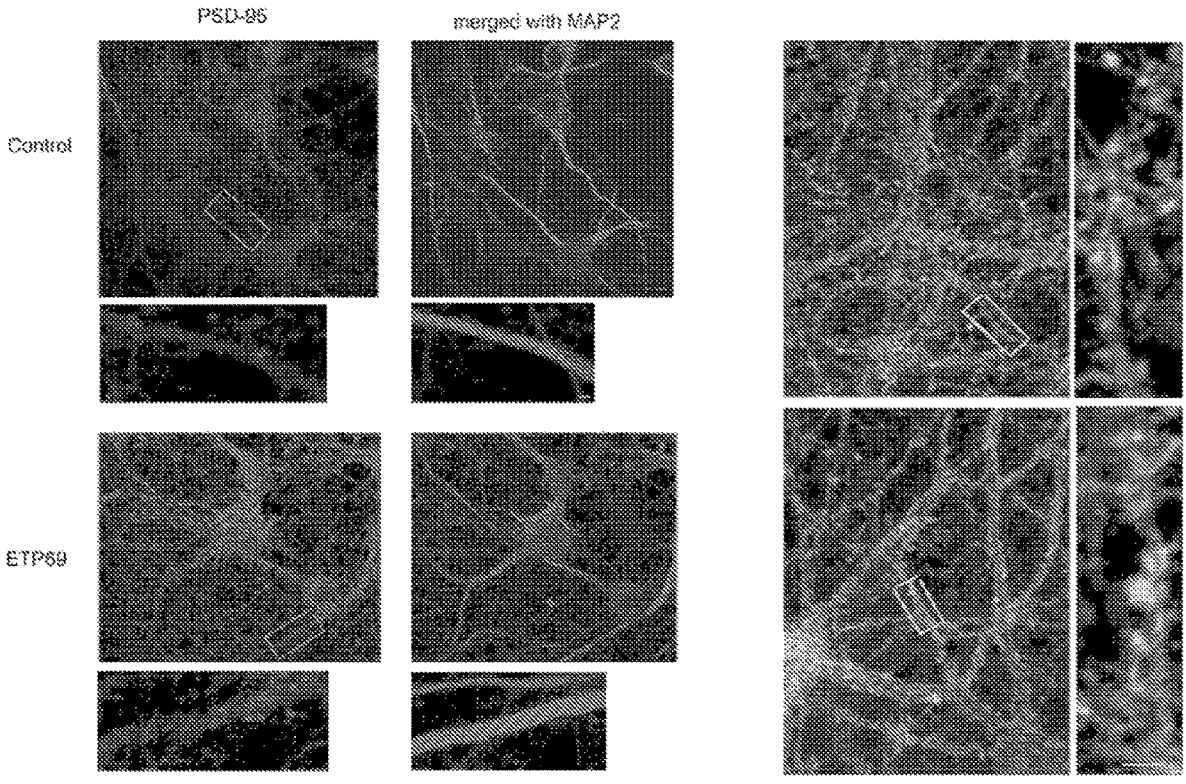
Figure 15A          Figure 15B

USE OF H3K9ME3 MODULATION FOR ENHANCING COGNITIVE FUNCTION

CROSS-REFERENCE TO RELATED APPLICATIONS

The present application is a continuation of U.S. application Ser. No. 17/697,893 which is a continuation of U.S. application Ser. No. 17/072,539, filed on Oct. 16, 2020, which is a continuation of U.S. application Ser. No. 16/354, 996, filed on Mar. 15, 2019, now U.S. Pat. No. 10,849,910, which is a continuation of U.S. application Ser. No. 15/580, 419, filed on Dec. 7, 2017, now U.S. Pat. No. 10,272,093, which is a U.S. National Phase of PCT/US2016/035764, filed on Jun. 3, 2016, which claims the benefit of U.S. Provisional Application Ser. No. 62/172,690, filed on Jun. 8, 2015, which is herein incorporated by reference for completeness of disclosure.

STATEMENT AS TO RIGHTS TO INVENTION MADE UNDER FEDERALLY SPONSORED RESEARCH AND DEVELOPMENT

This invention was made with government support under Grant No. AG000538 and AG012694 awarded by the National Institute of Health. The government has certain rights in the invention.

BACKGROUND OF THE INVENTION

Field of the Invention

Embodiments of the invention relates to treating cognitive dysfunction in aging, age-related and brain derived neurotrophic factor (BDNF)-dependent disorders. More specifically, the invention relates to treating cognitive dysfunction via administration of a SUV39H1 inhibitor referred to as ETP69 (Rac-(3S,6S,7S,8aS)-6-(benzo[d][1,3]dioxol-5-yl)-2,3,7-trimethyl-1,4-dioxohexahydro-6H-3,8a-epidithiopyr-rolo[1,2-a]pyrazine-7-carbonitrile) either alone, or in combination with other cognitive enhancers.

Description of the Related Art

Epigenetic dysregulation is known to contribute to several aspects of age related memory deficits. In the past few years many studies have identified changes in histone methylation states in aging. Methylation of the histone tail typically occurs at specific lysine residues, such as H3K4, H3K9, H3K27, H3K36, H3K79 and H4K20, and can either activate or repress transcription. In particular, trimethylation of H3K9 (H3K9me3) is an important repressive histone mark, and is implicated in gene silencing. Establishment of H3K9me3 depends on the activity of the histone methyl transferase SUV39H1 which regulates H3K9 trimethylation at the peri-centric heterochromatin.

While variations in H3K9 methylation have been suggested to be the underlying epigenetic mechanism for several age-related changes such as sustained vascular inflammation, diabetes, and metabolic memory, the direct effect of aging on regulation of histone lysine methylation in the brain has not been explored previously. Nor have there been any studies, which directly address the effect of SUV39H1 inhibition, and the corresponding downregulation of H3K9me3 on memory and cognitive function. Recent progress in the development of small molecule inhibitors of methyltransferases and demethylases which regulate the function of enzymes that contribute to histone methylation may thus be a powerful means to offset age-related deficits.

There is an urgent need to identify therapies and therapeutic regimes for cognitive dysfunction, e.g., cognitive deficits related to aging, aged-related disorders and Alzheimer's disease.

BRIEF SUMMARY OF THE INVENTION

One or more embodiments of the invention are directed to use of H3K9me3 modulation for enhancing cognitive function in aging and for treatment of age-related disorders, e.g. dementia and other defects related to brain and neural functions.

Some recent studies have revealed that histone methyltransferases and demethylases are implicated in aging and longevity. Methyltransferases catalyze histone methylation of specific genomic loci. And yet, how histone methylation contributes to learning and memory in aging has never been explored. Trimethylation of H3K9 (H3K9me3) is an important repressive histone mark, and is typically implicated in gene silencing. Embodiments of the present invention identify for the first time an essential role for histone H3K9me3 and its histone methyl transferase (SUV39H1) in mediating hippocampal memory functions. Pharmacological inhibition of SUV39H1 using a novel and selective inhibitor decreased levels of H3K9me3 in the hippocampus of aged animals, and improved performance in the object location memory task, fear conditioning task and in a complex spatial environment learning task. The inhibition of SUV39H1 induced an increase in spine density of thin and stubby but not mushroom spines in the hippocampus of aged animals and increased GluR1-containing AMPA receptors levels at spine surface, a key index of long-term potentiation (LTP).

In addition, there were changes at the BDNF gene promoter regions, in concert with overall BDNF protein levels in the hippocampus of drug treated animals compared with control animals. BDNF is a key member of the neurotrophin family, and is involved in a wide range of neurodegenerative diseases including mood disorders, depression, bipolar disorder and neuropsychiatric conditions such as schizophrenia, apart from aging. Through various processes such as dendritic arborization, synaptic consolidation, and strengthening TrkB signal transduction, BDNF serves neuronal plasticity, neuronal health and survival in the brain. The data presented here shows that SUV39H1 inhibition mediates BDNF regulation in the brain. Thus the compound may have utility in disorders in addition to those associated with age-related cognitive deficits where BDNF levels are inadequate to maintain normal performance including depression, schizophrenia, mood disorders and others. Together, these data demonstrate that SUV39H1 inhibition and the concomitant H3K9me3 downregulation mediates gene transcription in the hippocampus and reverses age-dependent deficits in hippocampal memory, and can be instrumental in reversing other BDNF-dependent disorders such as mentioned above but not limited to those above.

A spatial memory task, termed object location memory (OLM), which is known to be hippocampal dependent was used to evaluate the effects of H3K9me3 manipulation in aged animals. This was done to determine if ETP69 treatment differentially affects performance accuracy in the OLM task in a pre-trial versus a post-trial administration paradigm. The pre versus post-trial paradigms for the OLM task allows for testing of two distinct components of spatial memory formation. Specifically, the pre-training drug administration evaluates acquisition and recall of memory, while the post training drug administration targets memory consolidation and recall. It was found that intraperitoneal injection ("i.p.") of 10 mg/kg of the drug, administered either approximately 30 minutes prior to acquisition phase (pre-trial) or immediately after acquisition (post-trial) improved performance in the OLM task.

Another test of the effect of the compound on learning and memory utilized use of a task referred to as the unsupervised learning task (USL). The USL task is a behavioral paradigm in which mice are allowed to freely explore a four-compartment environment for a specified period of time. Reduction in overall activity and exploration of the test arena over this time is considered a measure of learning and short-term memory. If this occurs at similar rates in the two groups, it indicates no significant differences in short term learning and memory. We found that animals treated with ETP 69 (10 mg/kg; i.p.) showed a significant decrease in habituation/exploration (as measured by distance travelled) 24 hours after treatment. One-way ANOVA revealed significant group differences ($F_{3,19}$=4.05, p<0.05) and post hoc testing confirmed the difference between performance on Day 1 and Day 2 in ETP 69 treated animals (p<0.05) but not in the age matched control group.

In another test, using the contextual fear conditioning test, the compound was effective in improving hippocampal dependent learning and memory. We found that aged animals (n=7/group) that had been treated with ETP69 showed improved performance on the task compared to aged controls (p≤0.01).

Overall, these behavioral data suggest that ETP69 administration improves hippocampal-dependent learning and memory over a battery of tests. The data also suggest that other tasks which measure memory and cognitive performance may also be positively affected by administration of ETP69.

Since the OLM, fear conditioning and USL are all hippocampal specific task, the total level of H3K9me3 in the hippocampus following drug treatment in hippocampal tissue samples from the aged animals was also tested. The results showed significant effect of drug treatment in histone extracts obtained from the hippocampus of drug treated animals. T-test analysis showed decreases in H3K9me3 levels in animals treated with ETP69 (pre-trial, p<0.05).

Embodiments of the present invention provide the first evidence of a role of H3K9me3 in enhancing memory and cognitive function and show that this histone methylation mark can be reversed by a pharmacological intervention. The studies also provide evidence that by manipulating the enzyme that regulates histone methylation, it is possible to alter the chromatin state of subjects and restore memory function in the aging brain. Finally, this compound can be used alone or together with various lifestyle or pharmacological interventions to enhance cognitive performance. Cognitive function may be subdivided into and include subdomains such as memory (including working and episodic memory), learning, executive function, attention, speed of processing, and global cognitive functions such as activities of daily living, etc. The approach using a combination intervention may enhance cognition beyond either intervention alone.

BRIEF DESCRIPTION OF THE DRAWINGS

The above and other aspects, features and advantages of the invention will be more apparent from the following more particular description thereof, presented in conjunction with the following drawings wherein:

4

Figures 1, 2:
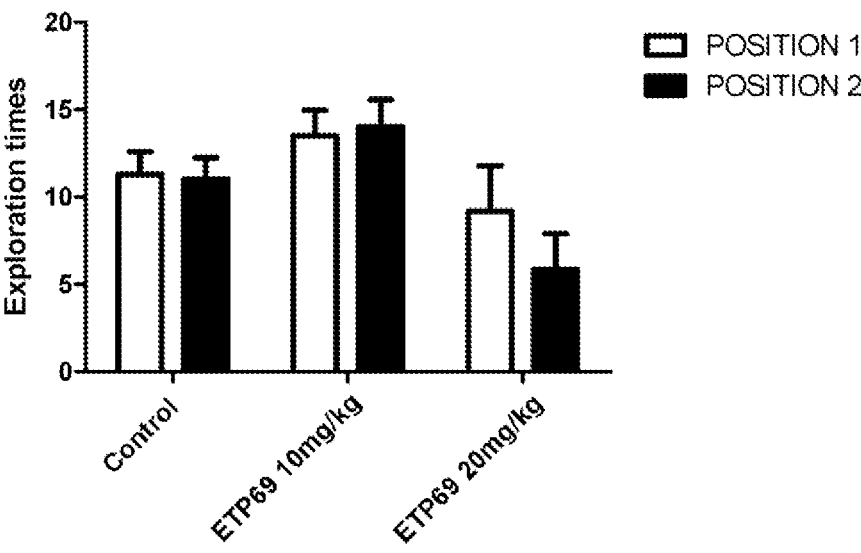

FIG. 1 illustrates the structure of ETP69 (Rac-(3S,6S,7S,8aS)-6-(benzo[d][1,3]dioxol-5-yl)-2,3,7-trimethyl-1,4-dioxohexahydro-6H-3,8a-epidithiopyrrolo[1,2-a]pyrazine-7-carbonitrile).

FIG. 2 is a graphical representation of the effect of the drug at 10 mg/kg and 20 mg/kg (i.p.) administered 30 minutes prior to acquisition phase in the novel place position task in mice.

FIG. 3 is a graphical representation of the results of OLM test showing the differences in exploration between mice treated with either vehicle, or 10 mg/kg of ETP69.

FIGS. 4A-B are graphical illustrations of the effect of the drug at 10 mg/kg (i.p) administered either 30 minutes prior to acquisition phase (Pre-Trial) or immediately after acquisition (Post-Trial) in the novel object location task in aged mice.

FIGS. 5A-B are graphical illustrations of the effect of the drug at 10 mg/kg (i.p) administered either 30 minutes prior to acquisition phase (Pre-Trial) or immediately after acquisition (Post-Trial) in the novel object location task in young mice.

FIG. 6A is a graphical representation of the effect of ETP69 in the unsupervised learning task.

FIG. 6B is a graphical representation of the effect of ETP69 in the unsupervised learning task.

Figure 7:
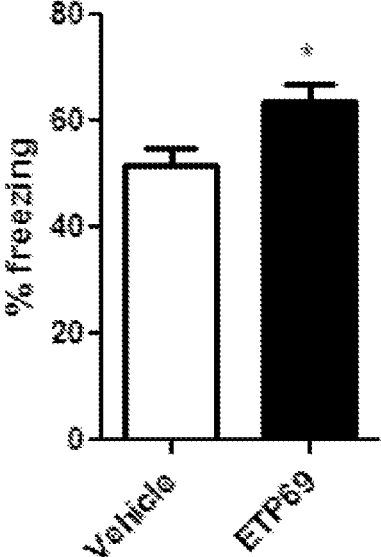

FIG. 7 is a graphical representation of the effect of ETP69 in the fear conditioning task.

FIG. 8A is a graphical illustration of trimethylation levels of H3K9 in hippocampal extracts of young vs aged mice.

FIG. 8B is a graphical illustration of trimethylation levels of H3K9 in cerebellum extracts of young vs aged mice, n=3/group, p<0.05.

FIG. 8C is a graphical representation of trimethylation levels of H3K9 in aged mice which had 10 mg/kg of the drug (i.p.) or vehicle, 24 hours post drug administration, n=7/group, *p<0.05.

FIGS. 9A-C are graphical illustrations of the effect of ETP69 treatment on spine counts (thin, mushroom and stubby) in the CA1 region of the hippocampus *p<0.05, significantly different compared to age-matched controls (Student's unpaired t test). **p<0.01, significantly different compared to age-matched controls (Student's unpaired t test).

Figure 10:
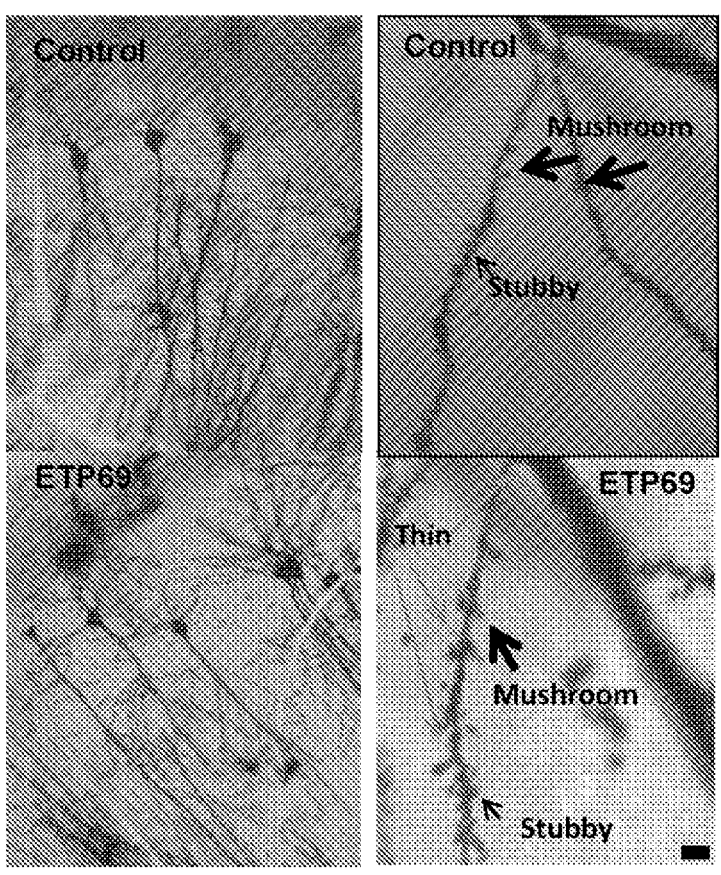

FIG. 10 presents representative images showing effect of ETP69 treatment on spines in the CA1 of the hippocampus.

Figure 11:
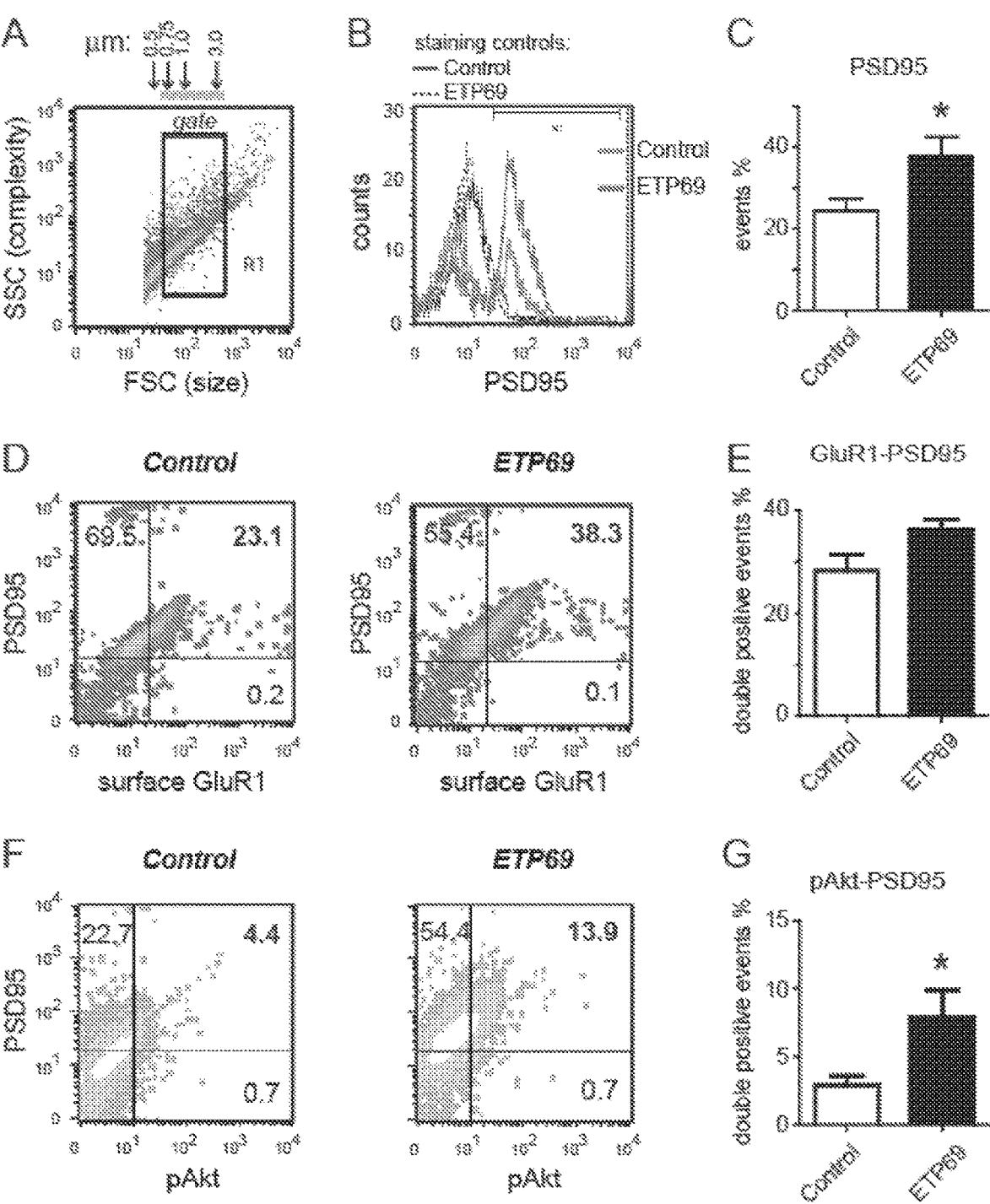

FIGS. 11 (A) Representative density plot showing size-gated synaptosomes; (B) Representative histogram showing an increase in the PSD-95 positive subpopulation of synaptosomes following ETP69 treatment; (C) PSD-95 positive events increase following ETP 69 treatment in synaptosomes obtained from aged mice; (D) Representative density plots showing surface GluR1 and PSD-95 expression in size-gated synaptosomes; (E) GluR1 and PSD-95 double-positive events (upper-right quadrant) increase following ETP 69 treatment in synaptosomes obtained from aged mice (p=0.05 vs. aged control mice); (F) Representative density plots showing pAkt and PSD-95 in size-gated synaptosomes. pAkt and PSD-95 double-positive events (upper-right quadrant) increase following ETP69 treatment; (G) pAkt and PSD-95 double-positive events increase following ETP 69 treatment in synaptosomes obtained from aged mice (p<0.05 vs. aged control mice).

FIG. 12A is a graphical illustration of BDNF protein levels in groups which had 10 mg/kg of the drug (i.p.) either 30 minutes before, or right after the acquisition phase in the OLM task are increased in the hippocampus compared to controls. p<0.01, significantly different compared to controls.

FIG. 12B is a graphical representation showing that H3K9me3 levels at Exon 1 of BDNF was significantly lower in ETP69 treated animals compared to controls (p=0.056). n=7 for controls and n=9 for ETP 69 treated animals.

FIG. 13 is a graphical illustration of the effect of ETP69 on neuronal survival after oxygen-glucose deprivation (OGD).

FIGS. 14A-B are illustrations of the effect of ETP69 on H3K9me3 levels in 14 DIV hippocampal neurons (A, gel image; B, quantification, n=3, *, p<0.05).

FIG. 15A are images showing ETP69 treatment (20 nM, 24 hours) increased PSD-95 immunoreactivity 14 DIV hippocampal neurons.

FIG. 15B are images showing ETP69 treatment (20 nM, 24 hours) increased dendritic F-actin staining (a marker of dendritic spines).

Figure 16:
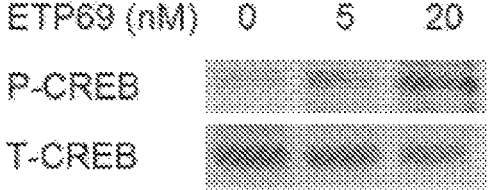

FIG. 16 is an image illustrating ETP69 increased CREB phosphorylation at Ser133 measured by Western blotting.

DETAILED DESCRIPTION

The present invention comprising use of H3K9me3 modulation for enhancing cognitive function will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an exemplary order to provide an understanding of one or more systems and methods, the exemplary order is not meant to be limiting. One of ordinary skill in the art would recognize that the steps or processes may be performed in a different order, and that one or more steps or processes may be performed simultaneously or in multiple process flows without departing from the spirit or the scope of the invention. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

For a better understanding of the disclosed embodiment, its operating advantages, and the specified object attained by its uses, reference should be made to the accompanying drawings and descriptive matter in which there are illustrated exemplary disclosed embodiments. The disclosed embodiments are not intended to be limited to the specific forms set forth herein. It is understood that various omissions and substitutions of equivalents are contemplated as circumstances may suggest or render expedient, but these are intended to cover the application or implementation.

The term "first", "second" and the like, herein do not denote any order, quantity or importance, but rather are used to distinguish one element from another, and the terms "a" and "an" herein do not denote a limitation of quantity, but rather denote the presence of at least one of the referenced item.

The term "dosage unit" as used herein refers to physically discrete units suitable as unitary dosages for animals, each unit containing a predetermined quantity of active material calculated to produce the desired therapeutic effect in association with the required diluent, e.g., a carrier or vehicle. The specifications for the unit dose of this invention are dictated by and are directly dependent on (a) the unique characteristics of the active material and (b) the limitations inherent in the art of compounding such active material for therapeutic use in animals.

The term "therapeutically effective amount" as used herein means that the amount of the SUV39H1 inhibitor compound of the present invention contained in the composition administered is of sufficient quantity to achieve the intended purpose, such as, in this case, to ameliorate cognitive deficits associated with aging, Alzheimer's disease, and other BDNF-dependent disorders. For the purpose of the present invention, treatment of age related cognitive defects may be measured by reversals or removal of the histone methylation mark. For example, by effectively regulating the function of enzymes that contribute to histone methylation, age-related cognitive deficits may be reversed.

Accordingly, by determining the increase in recall in a patient, one can readily determine whether the amount of the compound of the present invention is therapeutically effective. In one embodiment, the therapeutically effective amount of the compound ETP69 of the present invention may be, for example, 5 mg/kg, 10 mg/kg, 15 mg/kg, 20 mg/kg, 25 mg/kg, 30 mg/kg and other suitable values.

One or more embodiments of the invention provides methods to effectively ameliorate cognitive deficits associated with aging, Alzheimer's disease, and other BDNF-dependent disorders using in vivo inhibition of the histone methyl transferase SUV39H1 and the consequent trimethylation of histone H3K9 (H3K9me3) down regulation in the aging brain. H3K9me3 is an important repressive histone mark, and is implicated in gene silencing. Establishment of H3K9me3 depends on the activity of the histone methyl transferase SUV39H1 which regulates H3K9 trimethylation at the peri-centric heterochromatin. Regulating the function of enzymes that contribute to histone methylation may hence be a powerful means to offset age-related cognitive deficits. Cognitive deficits associated with aging, BDNF dysregulation, and other age related disorders involve deficits in processing sensory information, attention, acquisition and consolidation of memory, recall of information, and executive functions such as planning, problem-solving, inhibitory control, self-monitoring and other aspects of cognition that would relate to global functions among others.

In accordance with one or more embodiments of the present invention, the role of H3K9me3 in learning and memory in an animal model of aging using a newly developed analog of the epidithiodiketopiperazine alkaloid chaetocin A called ETP69, illustrated in FIG. 1, is studied. This compound, i.e. ETP69, a selective inhibitor of histone methyltransferase SUV39H1, shows significantly greater selectivity against a panel of 17 human histone methytransferases than chaetocin A, the first reported inhibitor of SUV39H1. In addition, ETP69 exhibits no inhibitory activity towards histone acetyltransferase p300 and DNA methyltransferase DNMT1.

The hippocampus is critically important for mammalian memory and is known to be compromised in the aging brain. The data are unequivocal that hippocampal impairment results in severe deficits in spatial memory. It has also been suggested that these findings could mean that spatial memory has singular status with respect to hippocampal function. Thus the studies for this invention used a spatial memory task to evaluate the effects of H3K9me3 manipulation in aged animals. In addition, the study employs a spontaneous activity task, referred to as the unsupervised learning task to extend and confirm these findings. This task measures hippocampal-dependent learning, is known to be highly correlated with synaptic changes in the hippocampus, and is susceptible to age related deficits. Also, another test that has been employed to measure the efficacy of the compound is the fear conditioning task. This task measures a form of learning and memory in which an aversive stimulus (e.g. an electrical shock) is associated with a particular neutral context (e.g., a room) resulting in the expression of fear responses to the originally neutral stimulus or context. It is also anticipated that other such tasks probing learning and memory would also benefit from the drug.

Then in order to identify the downstream cellular/molecular events underlying memory improvements by H3K9me3 inhibition, the study evaluated the effect of ETP69 on hippocampal spine formation using Golgi staining and flow synaptometry. In accordance with the essential role of BDNF on activity-dependent spine restructuring, studies of the effect of ETP69 on H3K9 trimethylation of bdnf exons and protein levels in hippocampus, along with Akt activation—a BDNF downstream effector—in synapses the data reveal a novel role for H3K9me3 in memory function and suggest a specific role in hippocampal dependent memory and learning.

Materials and Methods

Animals:

Aged (18-20 months, n=34) or young (3-4 months, n=18) C57Bl/6J male mice were group housed with food and water ad libitum, and were acclimated to the vivarium for one week before experimental procedures. Lights were maintained on a 12:12 light/dark cycle, and all behavior testing was carried out during the light phase of the cycle.

Compound:

ETP69 (Rac-(3S,6S,7S,8aS)-6-(benzo[d][1,3]dioxol-5-yl)-2,3,7-trimethyl-1,4-dioxohexahydro-6H-3,8a-epidithio-pyrrolo[1,2-a]pyrazine-7-carbonitrile), a racemic analog of epidithiodiketopiperazine alkaloids such as chaetocin A, was prepared as described in Overman LE, Baumann M, S., Nam D, Horne R, Jove L J, Xie C, Kwolik (2014) "Preparation of Epipolythiodioxopiperazine ETP Derivatives for Treatment of Cancer," PCT Int., vol. 2014066435, (Int, P., ed), USA [now also published in: M. Baumann, A. P. Dieskau, B. M. Loertscher, M. C. Walton, S. Nam, J. Xie, D. Horne, and Larry E. Overman "Tricyclic Analogues of Epidithiodioxopiperazine Alkaloids with Promising In Vitro and In Vivo Antitumor Activity," *Chemical Science*, 2015, 6, DOI: 10.1039/C5SC01536G, which is incorporated herein by reference in its entirety, and recrystallized from methanol. See also PCT Patent Application No. PCT/US2013/066252, entitled "ETP Derivatives," by Overman et al, which is also incorporated herein by reference in its entirety. The compound was dissolved in a mixture of 50% DMSO based saline solution. Control subjects received DMSO based saline solution.

Analogs of ETP69 would include compounds having the formula:

(I)

The symbol p is 2, 3 or 4. $R^1$, $R^2$, $R^3$, $R^4$, $R^5$, $R^6$, $R^{16}$, and $R^8$ are independently hydrogen, halogen, $-N_3$, $-CF_3$, $-CCl_3$, $-CBr_3$, $-Cl_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Testing:

Object Location Memory (OLM): Training and testing procedures were performed using a standard OLM protocol. Briefly, 22 aged mice and 18 young mice were handled for about 2-3 minutes per day for 5 days, followed by habituation to the experimental apparatus (white rectangular open field measuring 30×23×21.5 cm) for 5 min per day for 5 consecutive days before training.

Dose Response in OLM: On the test day mice were given 3 minutes of habituation (in an empty test arena) followed by i.p. injection of ETP69 (10 mg/kg (n=8) or 20 mg/kg (n=7)) or vehicle (n=7). Mice were then given a 3-min acquisition trial (with 2 similar objects placed in the arena opposite each other) 30 minutes after the i.p. injection of drug or vehicle and all animals were then returned to their home cages for a 24 hour inter-trial interval. Twenty-four hours later, a 3-minute retention test was administered, where one object was moved to a novel location and the amount of time the animals spent exploring the novel versus familiar location was recorded in order to evaluate the dose response in the OLM task. Since animals that had received 10 mg/kg performed better than other groups in the OLM task, 10 mg/kg was used for the remainder of the study. This OLM paradigm has previously shown to be subthreshold for learning.

Acquisition (pre-training) or Consolidation (post-training): In another test, aimed to determine the efficacy of the compound in pre and post training paradigms, the same group of 22 aged animals were retested on the OLM task 3 weeks after the first test. To determine whether the drug impacted acquisition or consolidation mechanisms, mice were injected with the 10 mg/kg compound (i.p. n=7) or vehicle (n=8). Animals were sacrificed right after retention testing (i.e. 24 hours post injection), and hippocampi were removed, rapidly frozen on dry ice, and stored at −80° C. until processing for trimethylation levels and BDNF assay. FIG. 2 is a graphical representation of the effect of the drug at 10 mg/kg and 20 mg/kg (i.p) administered 30 minutes prior to acquisition phase in the novel place position task in mice. The shows that mice treated with ETP69 at 10 mg/kg and 20 mg/kg (i.p.) administered 30 minutes before acquisition phase in the OLM showed no difference in object exploration (measured in seconds) in the acquisition phase. Data are mean±SEM; n=7 or 8/group.

18 young mice were also tested in the same OLM paradigm as described above. To determine whether the drug impacted acquisition or consolidation mechanisms, the young mice were injected with the 10 mg/kg compound or vehicle (i.p, n=6/group), either just before or right after the acquisition trial, and tested 24 hours post-acquisition. FIG. 3 is a graphical representation of the results of OLM test showing the differences in exploration between mice treated with either vehicle, or 10 mg/kg of ETP69. The data shows that in the retention phase of the task (24 hours after drug administration), mice treated with 10 mg/kg of ETP69 (i.p.) explored the novel object significantly (measured in seconds) more than the familiar object (**p<0.01, Bonferroni t test). Mice treated with 20 mg/kg of ETP69 performed similar to aged controls. Data are mean±SEM; n=7 or 8/group.

Unsupervised learning task: A new group of 12 aged animals were used for the unsupervised learning task. Procedures were adapted from published work. The unsupervised learning (USL) behavioral apparatus consisted of a large open field divided by walls into 4 chambers, all accessible by small entrances in each dividing wall. The animals can also access a smaller attached enclosed dark compartment by an open entrance. After 5 days of handling, animals were injected with ETP69 (10 mg/kg, i.p.) or vehicle and placed in the video-monitored USL box for thirty minutes, and the returned to the home cage. 24 hours later the animals were placed in the USL box again and euthanized immediately after. Their brains were rapidly removed, hippocampus dissected rapidly, frozen on dry ice, and stored at −80° C. until further processing Fear conditioning: 14 aged (18-20 months) male mice were placed in the fear-conditioning chamber were allowed to explore for 2 minutes before receiving one electric foot shocks (2 seconds, 0.2 mA). Animals were returned to the home cage 2 minutes after the foot shock. Twenty-four hours later, behavior in the conditioning chamber was observed for 5 minutes and subsequently was analyzed for freezing behavior, which was defined as the absence of all movement except for respiration.

Histone Trimethylation: Total histone was extracted from frozen hippocampi of 3 young and 3 old mice using an EpiQuik extraction kit (OP-0006-100) following the manufacturer's protocol. In brief, tissue was weighed and cut into small pieces and homogenized in 1× prelysis buffer, transferred in a 2-ml tube, and centrifuged at 10,000 g for 1 minute at 4° C. The supernatant was removed; tissue pellet was resuspended in 3 volumes of lysis buffer, incubated on ice for 30 minutes, and centrifuged at 12,000 g for 5 minutes at 4° C. Balance-dithiothreitol (DTT) buffer (0.3 volumes) was added to the supernatant, which was stored at −80° C. The protein concentration of the eluted histone was estimated using a Bradford protein detection kit (Bio-Rad, Hercules, CA) using BSA as a standard. Histone (H3K9) trimethylation analysis was performed according to manufacturer's information (ab 115064). Briefly, trimethylated histones were captured using specific antibody and detected with a labeled detection antibody, followed by a color development reagent. Absorbance was read at 450 nm, and results were calculated using a standard curve following the manufacturer's instructions.

Spine counts: In another series of experiments 10 aged mice (20-22 months) were injected with ETP69 (10 mg/kg; i.p) or vehicle (i.p) and 24 hours later the animals were euthanized and the brains were separated into two hemispheres. Right hemisphere was used for Golgi staining and the left was processed for flow synaptometry. Staining was conducted according to manufacturer's information (Golgi-Cox, Bioenna).

Flow Synaptometry: Fresh synaptosome P2 fractions were obtained from whole mouse hippocampus using our long-standing protocol. Briefly, the fractions were obtained from the hippocampus by homogenizing tissue (1:10 w/v) in ice-cold sucrose 320 mM. All the steps were carried out at 4° C.; sucrose buffer, grinder, pestle and microfuge tubes were all pre-cooled on ice. Hippocampi were rapidly dissected from a single mouse and homogenized in 320 mM sucrose (1.5 ml) containing HEPES [10 mM] and protease/phosphatase inhibitors cocktail, pH 7.4. Homogenization consisted of 6-8 manual strokes in a glass-Teflon grinder, clearance (between plunger and glass): 0.15-0.25 mm. Plunger was gently rotated during strokes while the grinder was kept on ice. The homogenate was centrifuged at 1200 g for 10 min. Supernatant (S1, containing mitochondria and synaptosomes) was transferred into two clean microfuge tubes and centrifuged at 12,000 g for 20 min. Supernatants (S2) were carefully removed using a plastic tip and vacuum. Pellets (P2, corresponding to the crude synaptosome fraction) were resuspended by gently pipetting up and down in 1.5 ml of PBS Protein concentration was determined using the BCA assay using bovine serum albumin (BSA) as standard. Before immunolabeling, all samples were adjusted to the same protein concentration using PBS as diluent. Immunolabeling for flow synaptometry analysis was performed according to a method for staining of extracellular/intracellular antigens using 200 ul of synaptosomal fractions (50-100 μg protein). Antibodies: GluR1 (extracellular) (Millipore, ABN241, DIL=1:400), p-Akt-ser473 (Cell Signaling, 4060, DIL=1:400), PSD-95 (Millipore, MAB1598, DIL=1:400), anti-rabbit IgG Alexa-488 ad anti-mouse IgG Alexa 647 (Life Science, DIL=1:400). Data were acquired using a FACS Calibur flow cytometer (BD Biosciences) equipped with argon 488 nm and helium-neon 635 nm lasers. Relative size and granularity was determined by forward (FSC) and side scatter (SSC) properties. FSC, SSC, FL1 and FL4 signals were collected using log amplification. Alexa 488 and Alexa 647 fluorochromes were detected by the FL1 and FL4 detectors, respectively. FSC-SSC plots were used to select particles matching the size of synaptosomes (0.5-3.0 μm) using calibrated beads (FIG. 6A). Identical FSC settings were used for acquiring data on bead standards and samples. Small fragments and debris were excluded by establishing a FSC-H threshold (325). Ten thousand size-gated particles were collected and analyzed for each sample. Analysis was performed using the CellQuest Pro software (BD Biosciences).

ELISA for BDNF

ELISA was performed using the BDNF Emax Immunoassay System (G7610, Promega) according to the manufacturer's instructions. Two sets of samples were prepared from the hippocampus of each animal, and all reactions were performed in duplicate.

The first series of experiments established that BDNF was a target of ETP69, then brains obtained from a second set of experiments (USL task) were used to detect which BDNF exons were methylated and which downstream targets of BDNF showed changes following ETP69 treatment.

ChIP for BDNF promoter regions: After cross-linking with 1% formaldehyde, chromatin was sheared to fragments of 200-500 bp. Immunoprecipitation was realized overnight at 4° C. with an antibody directed against histone H3K9me3 (H3K9me3; Millipore). After washes, elution from beads, and reversal of the cross-link, immunoprecipitated DNA was purified and analyzed in triplicate by qRT-PCR with an internal standard curve prepared from pooled input samples. Each sample was normalized with the respective input value. Primers for bdnf promoters for exon I, IV, and VI correspond to each unique exon sequence. RT-qPCR primer sets were designed using the Roche Universal Probe Library Assay Design Center and obtained from Integrated DNA Technologies (Coralville, IA). RT-qPCR reactions were run in a Stratagene MX3005P thermocycler at 95° C. for 3 min, followed by 45 cycles of 95° C. for 10 s, and 58° C. for 15 s. Each RT-qPCR run included all samples run in triplicate and a standard curve. Data were analyzed by the $2^{-\Delta\Delta ct}$ method and expressed as fold change over control after normalizing with input samples, as described previously.

Statistical Analysis

Mann-Whitney tests were used as non-parametric t-test for paired and unpaired data, respectively and Student test was used for parametric data. One way ANOVAs were followed by post hoc Tukey's test for mean comparisons of three or more groups; whereas two-way ANOVAs were followed by Bonferroni's post hoc test. All statistical tests and the non-linear fit for FIG. 6B were performed using GraphPad Prism 6. Data are presented as mean±SEM. p value<0.05 was considered significant.

Results

ETP69 in the Object Location Memory (OLM) Task

A dose-response study of the acute effects of intraperitoneally administered ETP69 in the spatial, OLM task, was conducted. The dose range included amounts known to be well tolerated in mice. Our results demonstrated that 10 mg/kg but not 20 mg/kg induced memory improvements in the OLM task in aged mice. This was confirmed using a two-way ANOVA (interaction effect, $(F_{(2,19)}=10.25$, p<0.01, n=7-8/group)), with post-hoc testing showing that the group receiving 10 mg/kg of the drug performed significantly better compared to controls (p<0.05, Bonferroni t-test). This is also reflected in the acquisition trial analysis. The acquisition phase of the testing showed no significant interaction effect ($F_{(2,19)}=0.139$, p=NS, n=7-8/group) or main effect of object location ($F_{(1,19)}=0.19$, p=NS). However, there was a significant treatment effect ($F_{(2,19)}=3.18$, p<0.05) with animals that had been given a higher dose of the drug (20 mg/kg) showing a decrease in total exploration time (p<0.05, Bonferroni t-test). This suggests that higher doses of the H3K9me3 may impair overall exploration and possibly impair locomotor activity in aged animals, so that optimal doses should be carefully identified Next, the studies sought to determine if ETP69 treatment differentially affects performance accuracy in the OLM task in a pre-trial versus a post-trial administration paradigm. The pre versus post-trial paradigms for the OLM task allow for testing of two distinct components of memory formation. Specifically, the pre-training drug administration evaluates acquisition and recall of memory, while the post training drug administration targets memory consolidation and recall. Thus, we administered the drug either 30 minutes before, or immediately after the acquisition phase of the OLM test. We found that 10 mg/kg (i.p) of the drug, administered either 30 minutes prior to acquisition phase (pre-trial, n=6/group) or immediately after acquisition (post-trial, n=8/group) improved performance in the OLM task (interaction effect ($F_{(2,19)}=9.81$, p<0.01, FIG. 4b). Further post-hoc testing showed a significant effect in both the pre and post-trial groups (p<0.001, Bonferroni t-test). The acquisition phase of the testing, showed no significant group differences (interaction $F_{(2,19)}=0.26$, main effect of drug $F_{2,19}=0.01$, main effect of object location $F_{(1,19)}=0.01$, p=NS, FIG. 4a).

FIGS. 4A-B are graphical illustrations of the effect of the drug at 10 mg/kg (i.p) administered either 30 minutes prior to acquisition phase (Pre-Trial) or immediately after acquisition (Post-Trial) in the novel object location task in aged mice. No difference in object exploration in the acquisition phase (A). In the retention phase of the task (24 hrs±30 minutes, post drug administration), drug treated animals explored the novel object significantly more than the familiar object (B)p<0.001, significant difference in time spent exploring novel versus familiar object.

To test the hypothesis that H3K9me3 inhibition positively impacts memory in young and aged mice, the behavioral testing was extended to young mice. Unlike in aged animals, administration of ETP69 did not improve OLM performance in young mice. 10 mg/kg (i.p) of the drug, administered either 30 minutes prior to acquisition phase (pre-trial) or immediately after acquisition (post-trial) did not show any statistical differences compared to young controls (interaction effect ($F_{(2,15)}=0.32$, p=NS, main effect of drug $F_{2,15}=2.21$, main effect of object location $F_{(2,15)}=6.02$, p<00.05, FIG. 5B, n=6/group). The acquisition phase of the testing also showed no significant group differences (interaction $F_{(2,15)}=0.44$, main effect of drug $F_{(2,15)}=25.01$, p<0.01, n=6/group) but no difference between exploration of POSITION 1 versus POSITION 2 (measured by Bonferroni t-test, p=NS, main effect of object location $F_{(2,15)}=1.56$, FIG. 5A). This suggests that H3K9me3 manipulation may have quite different effects in the young versus aged brain.

FIGS. 5A-B are graphical illustrations of the effect of the drug at 10 mg/kg (i.p) administered either 30 minutes prior to acquisition phase (Pre-Trial) or immediately after acquisition (Post-Trial) in the novel object location task in young mice. No difference in object exploration in the acquisition phase (A) or retention phase of the task (B) (24 hrs±30 minutes, post drug administration).

ETP69 in the Unsupervised Learning Task (USL)

To evaluate if H3K9me3 is implicated in measures of spatial learning and to evaluate molecular endpoints, a second series of experiments was conducted with the USL task being the behavioral endpoint. The USL task is a simple behavioral paradigm in which mice are allowed to freely explore a four-compartment environment for a specified period of time. Reduction in overall activity and exploration of the test arena over this time is considered a measure of learning and short-term memory. If this occurs at similar rates in the two groups, it indicates no significant differences in short term learning and memory. The locomotor pattern of mice reflects the habituation and learning they show, and is highly correlated with synaptic changes in the hippocampus.

FIG. 6A is a graphical representation of the effect of ETP 69 in the unsupervised learning task. While the aged mice continue to explore the test arena on both days, aged mice treated with ETP69 (10 mg/kg, i.p.) showed a significant decrease in habituation/exploration (as measured by distance travelled) on Day 2 compared with Day 1. Aged Control mice spent equal time(s) exploring the test arena on both Day 1 and Day 2. Habituation was measured over 30 minutes and data shown are in 5 minute bins *p<0.05, significant difference between habituation/exploration on Day 1 and Day 2 at the specified time points (Tukey's t test). n=5 or 6/group.

FIG. 6B is a graphical representation of the effect of ETP 69 in the unsupervised learning task. The graph shows the total distance travelled over 30 minutes on Day 1 and Day 2 following administration of ETP 69 (10 mg/kg, i.p.) or vehicle. *$p<0.05$, significant decrease in total distance travelled in 30 minutes between Day 1 and Day 2 (Tukey's t test). Data are mean±SEM; n=5 or 6/group.

During this test, well-handled mice were placed in the four-compartment test box and their movements were monitored for 30 min on Day 1 and then again 24 hours later on Day 2. It was determined that animals treated with ETP69 (10 mg/kg; i.p.) showed a significant decrease in habituation/exploration (as measured by distance travelled) 24 hours after treatment but not in the first 30 minutes on Day 1 (FIG. 6A). One-way ANOVA revealed significant group differences (F3,19=4.05, $p<0.05$) and post hoc testing confirmed the difference between performance on Day 1 and Day 2 in ETP69 treated animals ($p<0.05$) but not in the age matched control group (FIG. 6B, n=5/group). 30 min of exploration on Day 1 is sufficient to induce some long-term memory of the test arena in the mice and can be measured on the Day 2 of testing. We found a difference in activity levels on day 2 and interpret this as improved retention and recall in ETP69 treated animals even when learning remains the same between groups.

ETP69 in the Fear Conditioning Task

In another test, using the contextual fear conditioning test, the compound was effective in improving hippocampal dependent learning and memory. We found that aged animals (n=7/group) that had been treated with ETP69 showed improved performance on the task compared to aged controls (p≤0.01). Fear conditioning has been studied in numerous species and is often measured with freezing (a period of watchful immobility). A number of studies have shown that conditioned fear coincides substantially with the mechanisms of clinical anxiety disorders. Research into the acquisition, consolidation and extinction of conditioned fear suggests that this may be a means to treatments for an array of pathological conditions such as dissociation, panic attack disorder, phobias and even post-traumatic stress disorder in addition to learning and memory. In addition, it is known that the ventral medial Prefrontal Cortex (mPFC)—basomedial amygdala (BMA) projection implements top-down control of anxiety state and learned freezing, both at baseline and in stress-induced anxiety, defining a broadly relevant new top-down behavioral regulation pathway that is relevant for all the above mentioned conditions.

In order to confirm our findings from the OLM and USL tasks, we used the contextual fear conditioning to test the effect of H3K9me3 downregulation on hippocampal dependent learning and memory. Fear conditioning also indicates if amygdala and related functions are also regulated. We found that aged animals (n=7/group) that had been treated with ETP69 showed improved performance on the task compared to aged controls (p≤0.01). Overall, these behavioral data suggest that ETP69 administration improves hippocampal dependent learning and memory over a battery of tests.

FIG. 7 is a graphical representation of ETP6 in the fear conditioning task. Aged mice treated with ETP69 (10 mg/kg, i.p.) showed improved performance when contextual fear conditioning was assessed. *p=0.01, Bonferroni t-test, Data shown as ±SEM. n=7 per group.

H3K9me3 Levels in the Hippocampus

We first compared H3K9me3 levels in the hippocampus and cerebellum of young versus old mice and found significantly higher level of H3K9me3 in aged mice in the hippocampus but not in the cerebellum (FIG. 8A, $p<0.05$, n=3/group). Since the OLM and USL are both hippocampal specific task and we found a difference in H3K9me3 levels in the hippocampus of young versus old mice, we tested the total level of H3K9me3 in the hippocampus following drug treatment in hippocampal tissue samples from the cohort of animals described above in the OLM task. Our results showed significant effect of the drug in histone extracts from the hippocampus of the drug treated animals. t-test analysis showed decreases in H3K9me3 levels in animals treated with ETP69 ($p<0.05$, n=7/group, FIG. 8B). In comparison there was no significant difference between levels of H3K9me3 in the cerebellum of ETP69-treated versus untreated mice.

H3K9me3 Inhibition Increases Spine Density and GLuR1 Receptor Surface Expression in Hippocampal Synaptosomes It has been reported that novel memory formation can be associated with a transient increase in spine density in the hippocampus. In particular, improved performance in the OLM and USL tasks is associated with structural and/or functional changes at excitatory glutamatergic synapses. Thus, we examined whether pharmacological inhibition of the histone methyl transferase (SUV39H1) was sufficient to induce an increase in dendritic spine formation in the hippocampus.

Specifically, we counted and classified spines on CA1 pyramidal neurons. Dendrite segments from neurons in CA1 of the hippocampus were imaged by confocal microscopy and a blinded investigator counted and classified dendritic spines according to their morphology. Spines were manually counted and classified as thin, mushroom, or stubby, according to previously described criteria.

For each animal, at least 3 pyramidal neurons and 200 μm of total dendrite length and 250-500 spines were analyzed (n=5 animals per group). All of the neurons were chosen from the dorsal part of the CA1 hippocampal region (according with it essential role in spatial memory) and were completely stained along basal and apical dendrites. FIG. 10 presents representative images showing effect of ETP69 treatment on spines in the CA1 of the hippocampus. In this illustration, the top panel shows hippocampal neurons from control animals and the lower panel shows spines observed in ETP69 treated animals.

Segregation analysis was done to differentiate basal from apical dendrites in the same neuron. On average, ETP69 treated mice had 45% more total number of spines per length of dendrite (μm) compared to controls analysis of spine density by morphology revealed a significantly higher density of thin ($p<0.001$, Student's t-test), and stubby spines ($p<0.05$, Student's t-test), in ETP69 treated mice compared to control mice (FIGS. 9A-C). There was no difference in the numbers of mushroom spines/length of dendrite measured (FIGS. 9A-C).

Next, we studied the influence of ETP69 on synapses using flow synaptometry, an innovative approach to molecularly characterize isolated synaptosomes (presynaptic terminals attached to post-synaptic dendritic spines). We focus on the expression of PSD95 (scaffolding protein) and GluR1 (subunit of AMPA receptors), as the activity-dependent spine growth depends on the incorporation of AMPA receptor at PSD-enriched regions and this process links spine growth with increased synaptic transmission efficiency. After drug treatment, hippocampal synaptosome fractions were immunostained and analyzed by flow synaptometry. Sample acquisition by flow synaptometry first identifies synaptosomes by size using calibrated beads as previously described. It has been shown that the subset of particles between 0.5-3.0 μm is highly enriched in synaptosomes, as indicated by the high levels of synaptophysin and PSD95 in most (>70%) size-gated particles. Consistent with the ETP69-induced increase in spine numbers (FIGS. 9A-C), our analysis on size-gated particles revealed that ETP69 increases the proportion of synaptosomes expressing PSD95 ($p<0.05$, FIG. 11C), thus reflecting an increase in the number of synapses. No detectable changes were observed in the PSD95 levels per particle, as determined by the Mean Fluorescence of intensity. Next, we tested whether ETP69 increases the relative levels of spines expressing surface GluR1-AMPA receptors. We quantified the proportion of size-gated synaptosomes co-expressing GluR1 at surface and PSD95 intracellularly by double labeling combining extracelullar (no permeablization) and intracellular immunodetection. We found an increase in the amount of PSD95-positive (PSD95+) events co-expressing surface GluR1 in ETP69-treated mice, compared to vehicle-treated controls ($p=0.05$, FIG. 11E). Next, we analyzed the effects of ETP69 on Akt activation (Akt phosphorylation at Serine-473, p-Akt), an essential step for the activity-dependent transport of PSD95 to dendrites after NMDA receptor activation. According with the increased proportion of PSD95+GluR1+ events after ETP69 treatment, SUV39H1 inhibition by ETP69 also increased the proportion of events expressing both p-Akt and PSD-95 (p-Akt+PSD95+), relative to samples from vehicle-treated mice ($p<0.05$, FIG. 11G). Overall these results suggest that H3K9me3 inhibition acts, at least in part, by positively modulating molecular processes that promote spine generation and plasticity.

ETP69 Increases H3K9Me3 Levels at BDNF Promoter and BDNF Protein Levels in Hippocampus of Aged Mice It stands to reason that if treatment with SUV39H1 inhibitor stimulates spine formation in the hippocampus, it should also produce gene specific changes in distinct signaling cascades that correspond to memory. In the adult brain BDNF plays a major role on synapse formation and plasticity, acting at both pre- and postsynaptic sites. Thus we tested the effect of H3K9me3 downregulation on BDNF, which is critical for consolidation of hippocampal dependent learning and memory. The bdnf gene is composed of several noncoding exons, each one regulated by its own promoter and responding to different stimuli. We therefore evaluated whether ETP69 treatment decreases trimethylation of H3K9 at bdnf promoters I, IV, and VI. A significant effect of treatment was found for H3K9me3 at bdnf I ($p=0.05$, Mann-Whitney t-test, $n=7$ for control, 9 for ETP69, FIG. 12B). Importantly, ETP69-induced epigenetic changes at BDNF promoter were associated with an increase of BDNF protein levels in hippocampus. We found significantly elevated levels of BDNF in the hippocampus of ETP69 treated mice relative to controls ($p<0.01$ $F(2,16)=8.09$, ANOVA followed by post hoc Bonferroni t-test; FIG. 12A).

In this study we tested the potential of acute in vivo SUV39H1 inhibition and the consequent H3K9me3 down regulation to attenuate learning and memory deficits in aging. We further evaluated potential mechanisms which may contribute to cognitive benefits observed following H3K9me manipulation. Performance in the object location memory task, fear conditioning and the unsupervised learning task was improved following H3K9me3 downregulation. This corresponded with an increase in dendritic spine density of pyramidal neurons and an increase in synapses expressing surface GluR1-containing AMPA receptors in the hippocampus. Levels of BDNF were also upregulated in the hippocampus of animals which had been administered the SUV39H1 inhibitor, and synaptosomal extracts obtained from the hippocampi of these animals showed increased levels of phosphorylated Akt. These results therefore provide support for the amelioration of cognitive deficits and suggests that H3K9me3 downregulation triggers a cascade of events involving BDNF, spine remodeling and growth.

To the best of our knowledge, there have been no studies which have evaluated the effect of H3K9me3 inhibition on learning and/or memory function. Here, we present the first evidence that decreased H3K9me3 in the hippocampus improves spatial memory in aged mice. In both pre- and post-training paradigms of the OLM task, ETP69-treated animals performed equally well during testing, 24 hours post-acquisition trial. This led to the conclusion that acute treatment with ETP69 was inducing a hippocampus specific change in H3K9me3 levels in aged animals. Data from the USL task confirmed that ETP69 treated animals were showing improved retention and recall at 24 hours but not at 30 minutes post-drug treatment, when learning remained the same between groups. Repressors and cofactors recruited by H3K9me3 include histone deacetylases (HDACs) and heterochromatin protein-1α (HP1α). In fact, HP1 associates directly with SUV39H1 and leads to a self-sustaining repressive cycle and may require more than 30 minutes to show any behavioral manifestations. Thus the results are consistent with the hypothesis that changes at the molecular (and hence behavioral levels) are not rapidly engaged, but need time to evolve the mechanism supporting improved retention and recall.

Transient increases in spine density have been associated with improved learning and memory particularly in the hippocampus of aged mice, but the effect of H3K9me3 manipulation on synaptic function and spines is currently unexplored. Here we report that ETP69 increased both thin and stubby spine count in the CA1 region of ETP69 treated animals. Thin spines are flexible and critical for formation of new synapses which makes them well suited for facilitating acute improvements in cognition observed with ETP69-treatment. It stands to reason that the behavioral changes observed following H3K9me3 block was derived in part due to changes in spine density. Furthermore, remodeling spines requires incorporation of AMPA receptor at PSD-enriched regions (Park et al., 2004). It has been previously shown that synaptic connections can be strengthened by addition of AMPA receptor to synapses and that in fact it remodeling of spines requires the incorporation of AMPA receptors on synaptic surface. Our data show that levels of both PSD+ synaptosomes and the PSD95+ synaptosomes expressing surface GluR1 in synaptic terminals in hippocampal samples of ETP69 treated animal was increased, thus supporting the hypothesis that H3K9me3 mediates changes to synaptic network/signaling in the hippocampus leading to improved cognitive function in aging. In addition to its effect on the hippocampus, antagonism of H3K9me3 also leads to upregulation of p-AKT in size-gated PSD95-containing synaptosomes from the hippocampus. BDNF is a key molecule serving synaptic plasticity and neuronal activity. We have previously shown that HDAC inhibition in the aged brain improves spatial memory in a BDNF dependent manner. Since HDAC is one of the cofactors recruited by H3K9me3, we tested the role of SUV39H1 inhibition on BDNF protein levels in the aged brain. Our data show, that H3K9me3 modulates learning and memory and it is likely that this effect is mediated by a BDNF-dependent mechanism. Furthermore, our results suggest that EXON 1 alone, drives BDNF upregulation following ETP69 treatment in aged mice. It has been suggested that that differential production of BDNF transcripts may either affect the function of the protein, or provide a means for specific regulatory mechanisms in production of BDNF in different brain regions. It appears likely that H3K9me3 inhibition selectively participates in regulation of a BDNF transcript 1, but the downstream result of this selectivity remains unknown. However, we did not observe changes in Arc (data not shown). We cannot completely rule out the possibility that we did not observe changes in Arc because it is rapidly induced and decayed, but it is equally likely that there are multiple changes in synapses following H3K9me3 downregulation and Arc induction may not be one of them. This study only provides a first look at cascade of possibilities regulated either directly or indirectly by H3K9me3 inhibition. It is possible that activation of certain molecular pathway following removal of the H3K9me3 repressive mark activates hippocampal-memory pathway(s) which in turn may generate additional transcription and translation required for the maintenance of improved memory function in aged animals. The Effects of SUV39H1 Inhibitor ETP69 on Neuronal Survival and Functions We sought to establish that ETP69 can act directly on neurons. Unlike cancer cells neurons are non-dividing cells and thus are a distinct cellular target. We used primary neuronal cell cultures which are void of other cell types and where the concentration of drug can be rigorously controlled. Neuronal survival and synaptic growth is a common method to evaluate compounds.

OGD in 14 DIV hippocampal neurons was induced by an approach similar to that described by Newcomb-Fernandez et al (2001). Normal media was replaced with PBS and culture plates were placed in an airtight chamber. The chamber was flushed with $N_2$ and $CO_2$ for 3 minutes, sealed, and placed in a 37° C. incubator for 2 hours. PBS was replaced with DMEM (serum-free) and cultures were returned to a normoxic environment. Culture medium was collected 48 hours after the cultures had returned to a normal environment. The cytotoxicity was measured by LDH assay (Thermo-Fisher). To calculate % Cytotoxicity, subtract the LDH activity of the Spontaneous LDH, release Control (water-treated) from the chemical-treated sample LDH activity, divide by the total LDH activity [(Maximum LDH Release Control activity)—(Spontaneous LDH Release Control activity)], and multiply by 100:

$$\% \text{ Cytotoxicity} = \frac{\text{Compound-treated } LDH \text{ activity} - \text{Spontaneous } LDH \text{ activity}}{\text{Maximum } LDH \text{ activity} - \text{Spontaneous } LDH \text{ activity}} \times 100$$

Initially we tested the effect of ETP69 on oxygen-glucose deprivation (OGD)-induced cytotoxicity. Mature hippocampal neurons (14 DIV) were treated with OGD for 2 hours in the presence or absence of ETP69. Cytotoxicity was measured by LDH assay 48 hours after OGD. ETP69 at 4 nM but not 100 nM rescued neurons from OGD-induced cytotoxicity. FIG. 13 is a graphical illustration of the effect of ETP69 on neuronal survival after oxygen-glucose deprivation (OGD). 14 DIV hippocampal neurons were treated with OGD for 2 hours in the presence or absence of ETP. Cytotoxicity was measured by LDH assay 48 hours after OGD. Results are means±SEM of 4 samples. *, $p<0.05$.

Next, we examined the effect of ETP69 on H3K9me3 levels in cultured hippocampal neurons. 24 hours of ETP69 treatment resulted in a dose-dependent decrease in neuronal H3K9me3 level. FIGS. 14A-B are illustrations of the effect of ETP69 on H3K9me3 levels in 14 DIV hippocampal neurons (FIG. 14A—gel image; FIG. 14B—quantification, n=3, *, $p<0.05$). As the illustrations show, ETP69 treatment (24 hours) decreased H3K9me3 level measured by Western blotting.

As ETP69 at 20 nM led to greatest decrease in H3K9me3 level, we examined the effect of ETP69 at 20 nM on synaptic protein PSD-95 expression and morphology of dendritic spines. ETP69 treatment increased PSD-95 immunoreactivity. FIG. 15A are images showing ETP69 treatment (20 nM, 24 hours) increased PSD-95 immunoreactivity (a marker of dendritic spines where synapses are made) 14 DIV hippocampal neurons. Neurons were stained with antibodies against PSD-95 (red) and MAP2 (green). Scale bars: 10 μm, top panel; 2 μm, bottom panel.

FIG. 15B are images showing ETP69 treatment (20 nM, 24 hours) increased dendritic F-actin staining (a marker of dendritic spines). Note presence of numerous puncta marking presence of many spines. Top panel: Control, bottom panel: ETP treated neurons. Scale bar: 2 μm. This illustration shows that ETP69 also increased F-actin staining-labeled dendritic spines.

Furthermore, ETP69 treatment increased phosphorylation of transcription factor CREB at Ser133. FIG. 16 is an image illustrating ETP69 increased CREB phosphorylation at Ser133 measured by Western blotting. CREB is a transcription factor whose activation is involved in synaptic plasticity and memory formation.

These data distinguish the use of ETP on the nervous system and neurons from cancer applications as they demonstrate ETP69 acts on neurons, a non-dividing cell type, to promote their survival, growth and synaptic plasticity.

The studies provide evidence of the role of H3K9me3 in enhancing memory and cognitive function, e.g. age-related memory decline, and show that this histone methylation mark can be reversed by a pharmacological intervention. The studies also provide evidence that by manipulating the enzyme that regulates histone methylation, it is possible to alter the chromatin state of subjects and restore memory function in in the aging brain. Finally, this compound can be used alone or together with either various lifestyle interventions, or pharmacological interventions to enhance cognitive performance (i.e. cognitive enhancer), e.g. memory, learning, executive function, attention, speed of processing, global cognitive functions, activities of daily living, etc. These dual approaches may enhance cognition beyond either intervention alone. This will also lead to improved functional outcomes such as sleep, pain, and quality of life.

In one or more embodiments, pharmacological cognitive enhancers may include a cholinesterase inhibitor such as tacrine, donepezil, rivastigmine, and galantamine, for example. The pharmacological cognitive enhancer may also be an NMDA antagonist or an NMDA agonist, an ampakine, a BZD/GABA receptor complex modulator, a serotonin antagonist, a nicotinic class compound, a muscarinic class compound, a PDE inhibitor, a G protein class compound, a channel modulator, an immunotherapeutic class compound, an anti-amyloid or amyloid lowering agent, a statin or a PPARS modulator.

In one or more embodiments, lifestyle cognitive enhancers may include physical and mental exercises, dietary supplements such as antioxidant, a mitochondrial function enhancer, caffeine, omega-3, and Docosahexaenoic acid (DHA).

In one or more embodiments, the cognitive enhancer may include combinations of lifestyle and pharmacological interventions.

While the invention herein disclosed has been described by means of specific embodiments and applications thereof, numerous modifications and variations could be made thereto by those skilled in the art without departing from the scope of the invention set forth in the claims.

The invention claimed is:

1. A method of treating, preventing, or alleviating a cognitive dysfunction, comprising: administering to a subject suspected of having the cognitive dysfunction a therapeutically effective amount of a histone methylation inhibitor ETP69.

2. The method of claim 1, wherein the histone methylation inhibitor ETP69 inhibits a histone methyltransferase.

3. The method of claim 1, wherein the histone methylation inhibitor ETP69 inhibits histone lysine methylation.

4. The method of claim 1, wherein the histone methylation inhibitor ETP69 inhibits a histone trimethylation.

5. The method of claim 1, wherein the subject is a human.

6. The method of claim 1, wherein the histone methylation inhibitor ETP69 inhibits a histone 3 methylation.

7. The method of claim 1, wherein the histone methylation inhibitor ETP69 inhibits a histone 3 lysine 9 (H3K9) methylation.

8. The method of claim 1, wherein the histone methylation inhibitor ETP69 inhibits a H3K9 trimethylation (H3K9me3).

9. The method of claim 1, wherein the histone methylation inhibitor ETP69 does not significantly inhibit a histone acetyltransferase.

10. The method of claim 9, wherein the histone acetyltransferase comprises p300.

11. The method of claim 1, wherein the histone methylation inhibitor ETP69 does not significantly inhibit a DNA methyltransferase.

12. The method of claim 11, wherein the DNA methyltransferase comprises DMT1.

13. The method of claim 1, wherein the histone methylation inhibitor ETP69 is more selective against a methyltransferase than a chaetocin A.

14. The method of claim 1, wherein the histone methylation inhibitor ETP69 increases phosphorylation of a Akt or a CREB.

15. The method of claim 1, wherein the histone methylation inhibitor ETP69 is administered as a pharmaceutical composition.

16. The method of claim 15, wherein the administration prevents the cognitive dysfunction in the subject.

17. The method of claim 1, wherein the subject has the cognitive dysfunction.

18. The method of claim 17, wherein the administration slows, stops, or reverses the cognitive dysfunction in the subject.

19. The method of claim 1, wherein the administration improves neuronal survival or increases neuronal spine density in the subject.

20. The method of claim 1, wherein the administration improves memory in the subject.

* * * * *